United States Patent
Zubrägel

[11] Patent Number: 5,847,273
[45] Date of Patent: Dec. 8, 1998

[54] METHOD AND DEVICE FOR DETERMINING THE DELIVERED VOLUME OF A BATCH OR LOT OF BULK MATERIAL

[75] Inventor: Albert Zubrägel, Lohne, Germany

[73] Assignee: Albert Zubrägel Maschinenbau GmbH, Lohne, Germany

[21] Appl. No.: 954,786

[22] Filed: Oct. 21, 1997

[30] Foreign Application Priority Data

Oct. 22, 1996 [DE] Germany ................ 196 43 589.7

[51] Int. Cl.⁶ ........................................... G01F 23/00
[52] U.S. Cl. ................................................. 73/149
[58] Field of Search ........................ 73/149, 433, 861, 73/861.77, 861.78, 861.05

[56] References Cited

U.S. PATENT DOCUMENTS

| 5,121,638 | 6/1992 | Gmur ........................................ 73/861 |
| 5,351,558 | 10/1994 | Horn et al. .............................. 73/861 |
| 5,423,216 | 6/1995 | Kitamura et al. ...................... 73/433 |
| 5,665,910 | 9/1997 | Knutson et al. ........................ 73/149 |

FOREIGN PATENT DOCUMENTS

| 2087560 | 12/1971 | France . |
| 30724 | 1/1966 | Germany . |
| 2842816 | 4/1979 | Germany . |
| 8906721.5 | 7/1989 | Germany . |
| 4013246 | 10/1991 | Germany . |
| 4017652 | 12/1991 | Germany . |
| 89/11082 | 11/1989 | WIPO .................................... 73/861 |

*Primary Examiner*—Robert Raevis
*Attorney, Agent, or Firm*—Collard & Roe, P.C.

[57] ABSTRACT

A method and device for determining the delivered volume of a lot of bulk material, comprising collecting at least one sample from the lot, screening the sample, filling a measuring container with the screened sample, weighing the sample, determining the bulk density of the sample by dividing the measured weight of the sample by the volume of the measuring container, and dividing the weight of the lot by the bulk density to obtain the volume of the lot. The invention includes a device for performing the method comprising a mechanically-operated screening plant comprising a rolling screen. The screening plant screens several different grain fractions in one screening passage. A fine grain fraction is screened out first and each screened grain fraction is subsequently coarser than the preceding screened fraction. Each subsequent grain fraction is screened together with the overrun of the fraction collected in the preceding passage. Thus, the composition of the screened sample is representative of the lot.

9 Claims, 3 Drawing Sheets

METHOD AND DEVICE FOR DETERMINING THE DELIVERED VOLUME OF A BATCH OR LOT OF BULK MATERIAL

BACKGROUND OF THE INVENTION

1. Field of the Invention

The invention relates to a method for determining the delivered volume of a batch or lot of bulk material, for example, auxiliary soil materials and culture substrates. The method involves taking at least one sample from the batch or lot, screening the samples, and filling a measuring container having a predetermined volume with the screened samples. The content of the completely filled measuring container is then weighed, and the bulk density of the content of the measuring container is determined by dividing the weight of the content of the measuring container. Thus, the weight of the total lot is determined and the value of the weight of the lot is divided by the value of the bulk density of the content of the measuring container. The invention also relates to a device for carrying out this method.

2. The Prior Art

A batch or lot of auxiliary soil materials or culture substrates can be commercially traded in the form of a finished package or as a loose shipment. With known methods, the delivered volume of a lot has to be checked as provided by applicable standards, such as the draft of German standard DIN 11512-2 of April 1996. This standard prescribes the work steps for the determination of the delivered volume of a lot, which, by the known methods are carried out manually, using the following procedure:

When the lot is shipped in the loose form, samples are manually drawn at various points. With finished packages, samples are drawn manually from a number of packages. Each drawn sample is admitted to a first screen passage. The first part of the sample screened in this way is collected in a measuring container. The part of the sample with a coarser grain fraction not screened in the first screen passage subsequently passes through a second screen passage with a screen having a coarser particle size limit than the screen of the first screen passage. In other words, the portion of the sample screened in the respective screen passage is filled in the measuring container and the oversized grains not screened in the screen passage are subjected to a subsequent screening operation.

After all screening operations using screens with different particle size limits are completed, the measuring container contains a layer structure consisting of successively screened grain fractions of the sample. This layer structure results in a separation of the individual grain fractions and, therefore, de-mixes the sample, so that the sample is not representative of the composition of the total lot of the bulk material.

Under certain circumstances, the screening processes must be repeated a number of times in order to fill the measuring container with screened samples. This method increases the labor expenditure.

When the sample is screened manually, the large number of screens having different particle size limits increases the labor expenditure as well. Particularly with larger lots, the labor expenditure may rise to an undesirable amount due to the filling of a large number of measuring containers with screened samples. For this reason, generally only a few different screens are used. However, in this case, only certain grain fractions of the samples of the lot are screened or loosened up. The unscreened and loosened grain fractions of the lot are classified as overgrain and, in connection with the known methods, are to be deposited according to the DIN-specification in the measuring container as well. However, in practical applications, it is regularly seen that the overgrain is not crushed and then screened, but discarded in one way or another and consequently eliminated from the lot. This means that the screened samples are not representative of the lot to be delivered, as certain grain fractions are missing when the bulk density is determined, especially the fraction of so-called overgrain. As the screened samples serve as the basis for determining the delivered volume of the lot, the quality of volume determination may be adversely affected by the de-mixing of the samples as well as the missing grain fractions.

SUMMARY OF THE INVENTION

It is therefore an object of the invention to improve a method of the type specified above by reducing the labor intensity and enhancing the quality, and to make available a device for measuring the volume a lot of bulk material.

The method of the invention uses a mechanically-actuated screening device in the form of a rolling screen for screening the samples to screen different grain fractions in one screen passage. In the course of the screening passage, a fine grain fraction is screened off first and each screened fraction is subsequently screened together with the next-coarser grain fractions collected as overgrain in the preceding passage. The unscreened overgrain and the sifted grain fractions of the bulk material are subsequently filled in the measuring container as collected on the ejection side of the screening device.

The method according to the invention screens the samples in one screen passage. This one screen passage comprises treatment of the samples by first sifting out a fine grain fraction and subsequently sifting the screened grain fraction again, together with all remaining, i.e., still unscreened, coarser grain fractions. The second screening preferably takes place in a screening plane of the rolling screen device having a rolling or conveying direction opposite to the one of the preceding screening plane. This way, at the end of the entire screening passage, the samples are not collected in the form of individual, separated grain fractions. Consequently no de-mixing of the samples occurs, and the composition of the samples is representative of the total lot of the bulk material.

The method according to the invention is applicable not only in connection with auxiliary soil materials or culture substrates, but also for sawing and cutting chips, cat litter or the like.

Due to the fact that a mechanically-actuated screening device designed in the form of a rolling screen is used with the method according to the invention, a great number of samples can be intensively screened in a short time with reduced labor expenditure. The quality of the average bulk density of the lot, which is to be determined based on the bulk densities determined for the individual samples, is enhanced as well, which thus enhances the determination of the delivered volume of the lot. The rolling screens also have the advantage of achieving very intensive loosening, and thus increased screening quality. Breaking up the material is especially advantageous because precompressions caused by long storage, long shipping distances, inherent loading and the like are loosened again.

The samples of the lot admitted into the rolling-screen device are loosened in various stages and screened at the same time. Due to such loosening or elimination of precompression of the grain fractions of the samples, the amount of unscreenable overgrain is greatly reduced, and optimal screening of the admitted samples of the lot is achieved. The rolling-screen device advantageously delivers to the measuring container not only the screened grain fractions, but even the overgrain that can no longer be screened by a rolling-screen device. This means that the screened sample has a composition similar to the sample collected from the lot after it has been sifted.

The use of rotating screens has the further advantage that the drive of the rotating screens is controllable without problems. Therefore, the circumferential speed of the screen stars of the rolling screens can be adapted in each case to the given precompression and grain conditions.

The measuring container, which has a predetermined volume, can be completely filled by discontinuing the filling of the measuring container at a predetermined height of the pouring cone projecting beyond the edge of the opening of the measuring container. A leveling device is subsequently actuated for scraping off the excess material of the pouring cone. When the measuring container is adequately filled, the filling process is discontinued by a filling level sensor which may be coupled with the drive of the screening plant and/or the drive of the sample-collecting device. This causes the feed of additional samples into the measuring container to be stopped.

The relevant standard specification prescribes a defined compression of the bulk material contained in the measuring container. Due to the predetermined height of the pouring cone, a dead weight conforming to the height of the cone can advantageously obtain the specified compression of the bulk material contained in the measuring container. The portion scraped off from the sample of the lot to be shipped is added again to the lot, so that it is not missing.

One possibility for determining the weight of the contents of the measuring container is to first weigh the container with its contents after the excess has been scraped off, then determine the weight of the contents and subsequently empty the measuring container. The empty weight of the measuring container is determined with an electronic weighing device. Following complete filling of the measuring container, the weight of the container is determined by the weighing device again. The empty weight of the measuring container is then deducted from the weight of the filled measuring container, and the weight of the contents of the container is thus determined. The weighing device may be connected to a data processing facility, by which the net weights of the contents of the measuring container can be recorded in an advantageous way. Based on the net weights of the contents of the measuring container, the data processing facility can advantageously determine and recallably store a mean bulk density of the collected samples.

Another possibility for determining the weight of the contents of the measuring container is to empty the container after the pouring cone has been scraped off, and to weigh the emptied content. After the measuring container has been completely filled, the content is emptied onto a weighing device, for example an electronic weighing device, and the weight of the contents of the measuring container are determined. In this case too, the net weight of the contents can be recorded by a data processing system.

So that the screened samples of the lot are not missing, the content of the measuring container is added back to the lot after its weight has been determined, for example by simply emptying the container.

When the lot is delivered in the loose form, a loading process can be employed, in which the lot is gradually collected at its storage site and continuously conveyed to a loading station. The samples are then taken from the conveyed material at the loading station. The loose lot to be shipped can be conveyed off continuously and thus as quickly as possible, for example by a revolving loading belt. A weighing device can be installed on the loading belt for continuously recording the weight of the portions of the lot being loaded, so that the total weight of the lot is simultaneously determined with the loading operation and is determinable after loading has been completed.

The weighing system can also be advantageously connected to a central data processing facility. The data processing facility, with suitable programming, is capable of determining the bulk density of the content of the measuring container based on the recorded weight of the content of the measuring container and its known volume. As soon as the total weight of the lot has then been determined, for example immediately after the loading operation has been completed, the delivered volume of the loaded lot can be issued by the data processing facility.

The method according to the invention ensures safe and simple sample collection using a mechanically operated conveyor for collecting the samples, and dumping the collected samples from the conveyor into the screening device at the inlet of the screening device. During loading with the mechanically-operating conveyor, the samples are collected from the material conveyed by the loading belt without interfering with the loading operation. Due to the fact that the lot is continuously conveyed during loading, the collected samples represent samples collected from different points of the lot. This means that the sample selection is largely representative of the entire lot. The conveyor transports the collected samples and supplies them to the screening device. The controllable drive of the screening device and the drive of the conveyor can be coupled with the filling level sensor of the measuring container, so that the sample collection and/or screening can be simply discontinued when the measuring container is adequately filled. The loading operation, of course, can continue.

With extensive lots, the sample collection, screening and determination of their bulk density can be performed a number of times, such as during a longer-lasting loading operation. In this way, the quality of the determination of the delivered volume can be enhanced even further.

The invention further provides for a device for carrying out the method, comprising a mechanically-operated screening plant designed in the form of a multi-deck rolling screen for screening and mixing different grain fractions by one screen passage.

With the device according to the invention, screening of the samples can be carried out with less labor expenditure as compared to manual screening. The multi-deck rolling screen has a plurality of screening planes, consisting of shafts arranged in parallel. Several screen stars with star arms disposed radially relative to the shaft are arranged next to each other on each shaft. Due to the fact that the spacing between the screen stars of adjacent shafts is selectable and that the circumferential speed of the screen stars forming one sifting plane is controllable, a defined grain fraction can be advantageously sifted with each screen plane. The overgrain of the sample that is not siftable in a given sifting plane is transported by the rotating screen stars across the sifting plane and, like the sifted grain fraction, is received on the given next-following sifting plane. After passing through all sifting planes of the screening plant, any overgrain still present is finally collected like the sifted component of the sample, for example on the ejection side.

In this connection, the multi-deck rolling-screen plant is designed in such a way that each sifting plane has a rolling or conveying system moving in the opposite direction of the sifting plane preceding it.

The device further comprises a transport system for collecting the sifted samples from the ejection side of the screening plant and for feeding the samples into the inlet of a measuring container. The transport system may be a revolving conveyor belt. The conveyor belt, which is arranged below the screening plant, collects the ejected and sifted samples and the overgrain as well, and transports the samples and overgrain to the measuring container.

The control for filling the measuring container is advantageously designed so that a filling level sensor coupled with the drive of the screening plant is associated with the measuring container. The filling level sensor comprises a scanning device for scanning the height of the pouring cone. The filling level sensor may comprise an electronic circuit acting upon the drive of the screening plant, and dependent on the scanned height of the pouring cone. When a predetermined height of the pouring cone has been reached, further filling of the measuring container is interrupted by a suitable signal of the scanning device, such as by switching off the screening plant together with its conveyor belt. General interruption of the feed to the measuring container suffices for the purpose intended in this connection. It would also be possible to reverse the running direction of the conveyor belt, whereas the screening plant and the collection of samples continues to operate. However, in this case, the screened samples must be readmitted to the loading process during such interruption. The scanning device used can be a lever mechanism scanning the pouring cone, or also a contactless optoelectronic device such as, for example a light barrier.

To completely fill the measuring container, a scraping device actuated in dependence on the height of the pouring cone is provided. The scraping device scrapes off the projecting excess of the pouring cone at a level corresponding to the filling level when a predetermined filling volume of the measuring container is reached. After the measuring container has been filled, the scraping device is actuated, which is connected to the filling level sensor. The scraping element of the device is advantageously a rotating cutter. This rotating cutter can be guided across the edge of the opening of the measuring container via a mechanics in order to cut off the projecting part of the pouring cone. Of course, other types of the scraping elements are conceivable as well. However, a rotating cutter has the advantage that the contents of the measuring container are not compressed during scraping.

The device according to the invention preferably includes a collecting device for collecting the scraped-off part of the pouring cone and feeding the projecting part of the pouring cone back into the lot. This collecting device may be in the form of a funnel or trough or the like, so that the scraped-off or cut-off portion of the sample is collected and added again to the lot by simply letting it slide or drop into the lot.

The device also includes a weighing device such as an electronic scale for weighing the contents of the measuring container. The scale and the measuring container may be designed in the form of one unit, wherein the empty weight of the measuring container is then entered in an associated data processing facility as the subtrahend. It would also be conceivable to separate the scale from the measuring container and to empty the contents of the measuring container into the scale to determine the weight of the emptied contents of the measuring container.

So as to add the samples back into the lot, a discharging device for discharging the weighed contents of the measuring container are associated with the weighing device, and is actuated after the weight has been determined. The discharging device can be coupled with the weighing device or electronic scale, so that after the weight of the contents of the measuring container has been determined, the discharging device can be actuated and the weighed contents of the measuring container returned to the lot. The discharging device can be designed in the form of a tilting device arranged on the scale or on the measuring container.

Operationally safe and constructionally simple sample collection can be achieved with a sample collection device as part of the invention. The sample collection device is equipped with a conveyor for transporting the collected samples into the inlet of the screening plant and ejecting them into the inlet. The conveyor is a bucket mechanism with rotating buckets designed in the form of an endless conveyor. When a batch or lot is shipped or delivered in loose form, the samples can be simply collected with the mechanically-operated endless conveyor and its revolving buckets while the lot is being loaded.

To ship the lot in loose form, the device has a loading device for gradually collecting and loading the lot. A loading device is advantageous when shipping larger quantities in order to ensure quick loading of the lot with the least possible labor expenditure.

The loading device is preferably a loading belt. The use of a loading belt offers the possibility of transporting the lot to be loaded in a simple and quick way. Of course, other types of loading devices can be used as well.

The collection side of the sample collection device is advantageously associated with the transport route of the lot gradually collected at the storage site and transported off for loading. The route of the lot is determined by the transporting belt. In this way, each sample can be advantageously collected at different points of the lot. The collected samples consequently form a representative cross section of the composition of the total lot.

To determine of the delivered volume of the lot to be loaded, the loading device is equipped with a scale for continuously recording the weight of the portion of the lot being loaded at the given time. The scale continuously records the weight of the portion of the lot being transported via the loading belt and may be designed in the form of a conveyor belt scale connected to a central data processing system. The data processing facility computes a mean bulk density of the collected samples based on the previously determined weight of the content of the measuring container and the volume of the container. To determine the shipped volume of the lot, the value of the total weight of the lot is divided by the value of the mean bulk density. The determined volume of the lot can be recalled with the help of the data processing facility.

BRIEF DESCRIPTION OF THE DRAWINGS

Other objects and features of the present invention will become apparent from the following detailed description considered in connection with the accompanying drawings. It is to be understood, however, that the drawings are designed as an illustration only and not as a definition of the limits of the invention.

In the drawings, wherein similar reference characters denote similar elements throughout the several views.

DETAILED DESCRIPTION OF THE PREFERRED EMBODIMENT

Figure 1:
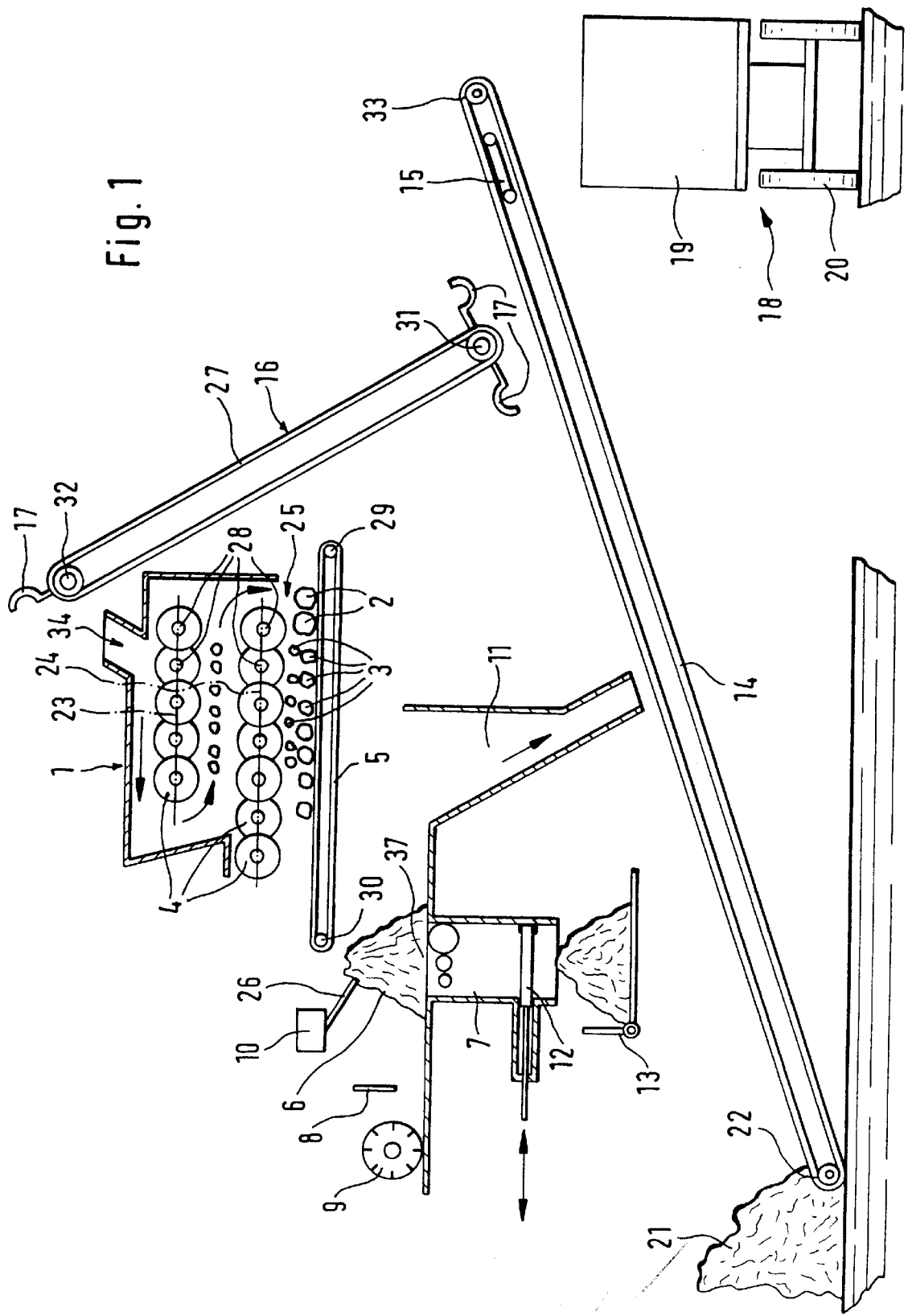
FIG. 1 is a schematic representation of a device for carrying out the method according to the invention.

Referring now in detail to the drawings and, in particular, FIG. 1, there is shown a schematic representation of a device according to the invention for determining delivered volume of a lot of bulk material such as, for example auxiliary soil materials and culture substrates. The device has a loading device for the gradual collection and loading of the lot, which is designed in the form of a loading belt 14. Loading belt 14 starts with its end 22 on the receiving side at a storage site 21 of the lot and ends with its end 33 at the discharging side at a loading site shown as truck 18. Truck 18, which is realized as the loading site, has an undercarriage 20 and a loading area in the form of container 19. A conveyor belt scale 15 continuously records the weight of the portion of the lot being loaded and is arranged within the zone of end 33 of transporting belt 14 on the discharge side.

A sample collection device 16 consists of an endless conveyor 27, which is equipped with revolving, radially projecting buckets 17. The length of the path of conveyance of endless conveyor 27 is limited by the lower reversing roller 31 as the collection zone, and the upper reversing roller 32 as the discharging zone. The lower reversing roller 31 is arranged with the collection zone of endless conveyor 27 within the range of the transport path determined by loading belt 14 for conveying the lot gradually collected at the storage site to the loading site.

Buckets 17 revolving on the lower reversing roller 31 are tangent to loading belt 14 in such a way that they collect samples from the gradually collected portion of the lot to be shipped as they are conveyed along loading belt 14. The samples picked up by buckets 17 are ejected into a screening plant 1 through an inlet 34 of screening plant 1. Buckets 17 are emptied as the upper reversing roller 32 is rotating. In the present case, screening plant 1 has an upper screening plane 23 and a lower screening plane 24.

Each of screening planes 23 and 24 are formed by shafts 28 arranged in parallel. Several screen stars 4 are mounted on each rotating shaft 28. The stars are indicated here as circles, but shown in greater detail in FIG. 2. Each screen star is equipped with screening star arms 35, 35', and 35", which project radially with respect to shaft 28, as shown in FIG. 3. The overlap zone 38 (not shown here) of star arms 35, 35' and 35" of screen stars 4 of adjacent shafts 28 determines the grain fraction of each screening plane 23 and 24 to be screened. Overlap zone 38 of star arms 35 is selectable by the dimension of star screens 4 and by the spacing of shafts 28.

The route of transport of the overgrain of the samples is indicated by arrows shown in screening plant 1. Overgrain 2 is ejected on ejection side 25, and the screened grain fractions 3 are ejected onto the transporting belt 5 arranged below screening plant 1. Transporting belt 5 extends across ejection side 25 of screening plant 1, whereby the length of transporting belt 5 is limited by a first reversing roller 29 and a second reversing roller 30 arranged within the zone of inlet side 37 of a measuring container 7.

Measuring container 7 has a predetermined volume and its bottom is designed in the form of a slide 12. When measuring container 7 is filled, a pouring cone 6 forms at the edge of the opening of measuring container 7. The filling process for filling measuring container 7 is controlled by a filling level sensor 10 that senses the height of the pouring cone projecting beyond the edge of the opening of measuring container 7. Filling level sensor 10 has a scanning device 26 scanning the height. Filling level sensor 10 is coupled with the drive of screening plant 1 and the drive of transport belt 5, so that when the predetermined volume of measuring container 7 is reached, screening plant 1 and/or transport belt 5 can be switched off.

A scraping device 8, which is coupled with filling level sensor 10, is arranged at the edge of the opening of measuring container 7 on inlet side 37 of the measuring container. Scraping device 8 has a scraping element in the form of a rotating cutter 9 for scraping off the projecting part of pouring cone 6 in a plane corresponding with the filling level of the measuring container after a predetermined volume of the filling of said container has been reached. The portion of pouring cone 6 cut off by cutter 9 is returned via a funnel-like collection device 11 to loading belt 14 by simply dropping onto the latter, and is thus added again to the lot.

By actuating slide 12 on the bottom side of measuring container 7, the contents of measuring container 7 can be loaded on an electronic scale 13 arranged beneath measuring container 7. Electronic scale 13 determines the weight of the content of measuring container 7. The weighed content of measuring container 7 can be tilted onto loading belt 14 by a tilting motion of scale 13. Electronic scale 13 is connected to a data processing facility (not shown). Such data processing facility can record the net weight of the content of measuring container 7 as determined in each case by scale 13, and store same in a recallable way. The net weight of the content of measuring container 7 is divided by the predetermined volume of measuring container 7. The bulk density of the contents of measuring container 7 follows from such division. Also, a mean bulk density can be determined when several measuring containers 7 are filled with screened samples of lot. Conveyer belt scale 15, which continuously records the weight of the part of the lot being loaded, is connected to the data processing facility as well, so that the delivered volume of the lot follows from the recorded total weight of the lot divided by the mean bulk density of the content of measuring container 7.

Figure 2:
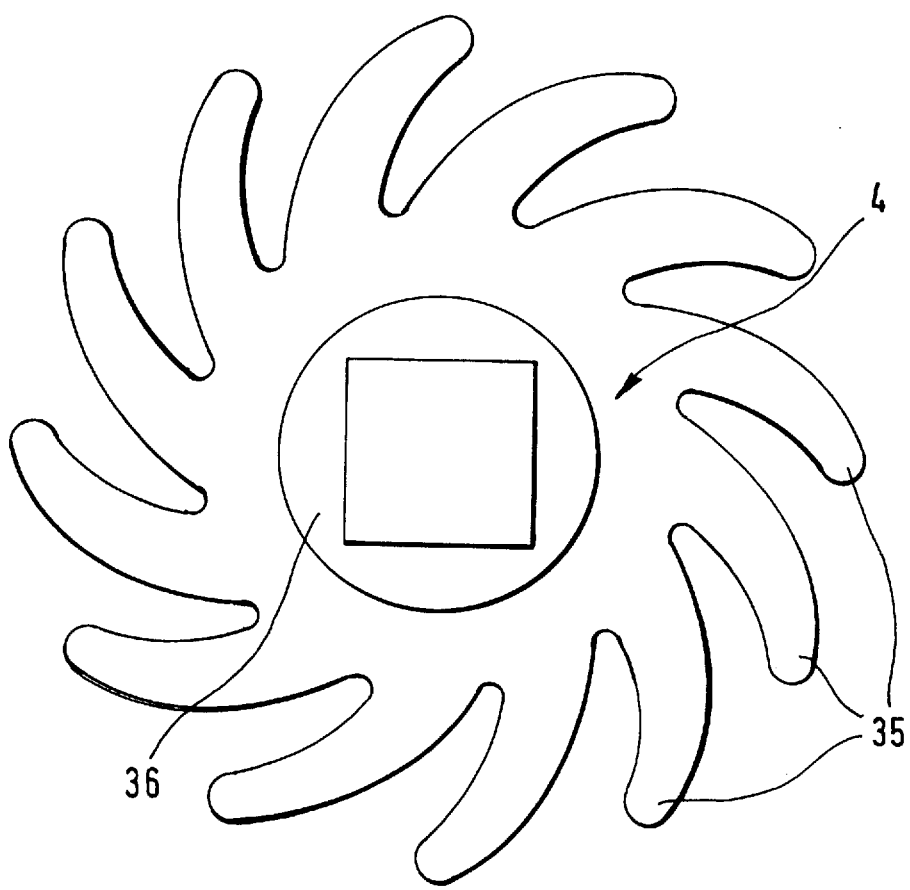
FIG. 2 shows an enlarged front view of a screen star of the screening plant contained in the device according to FIG. 1.
Figure 3:
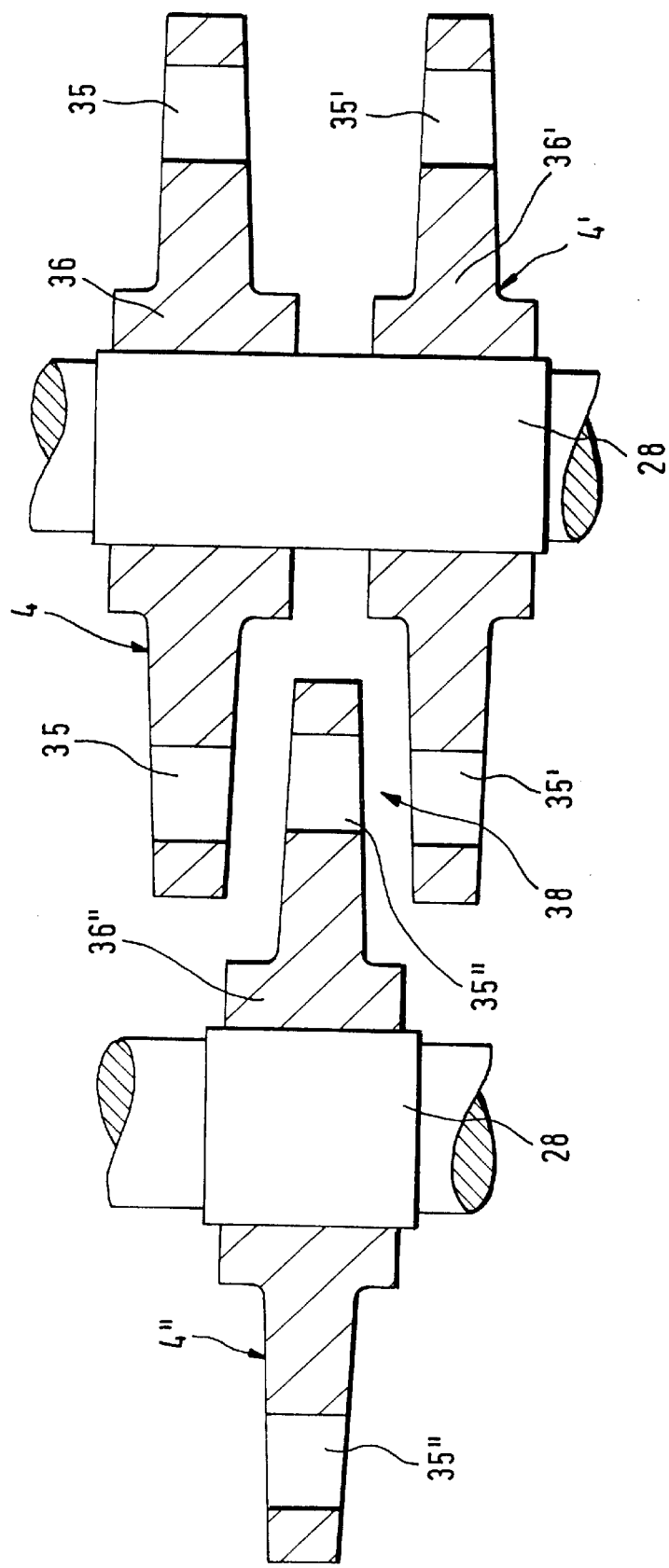
FIG. 3 shows a schematic front view of a detail of the screening plant with screen stars shown by sectional views.

FIG. 2 shows an enlarged front view of screen star 4 of screening plant 1. Screen star 4 has star arms 35 projecting across its circumference. A hub 36 fitting on shaft 28 is located in the center of the screen star.

FIG. 3 shows two adjacent shafts 28 of a screening plane 23 or 24 with the screen stars 4, 4' and 4" arranged thereon. Screen stars 4, 4' and 4" each are torsionally rigidly mounted on shafts 28 with their hubs 36, 36' and 36", respectively. Overlap zone 38 of screen arms 35, 35' and 35" is selectable by the dimension of screen stars 4, 4', and 4", and by the spacing of shafts 28. The size of overlap zone 38 of star arms 35, 35' and 35" determines the screenable grain fraction because the grain fractions to be screened are loosened in overlap zones 38 by the screen stars 4 rotating on shafts 28, and thereby screened.

Accordingly, while only one embodiment of the present invention has been shown and described, it is obvious that many changes and modifications may be made thereunto without departing from the spirit and scope of the invention.

What is claimed is:

1. A method for determining the delivered volume of a batch or lot of bulk material, comprising the steps of:

collecting at least one sample of material from the lot;

screening said at least one sample of material with a mechanically operated screening plant comprising a rolling screen, said screening plant screening several different grain fractions in one screening passage, each screened grain fraction having an overrun portion, wherein a fine grain fraction is screened out first and each screened grain fraction is subsequently coarser than the preceding screened fraction, and wherein each subsequent grain fraction is screened together with the overrun portion of the fraction collected in the preceding passage;

filling a measuring container having a predetermined volume with the screened sample of material, said measuring container having an inlet opening;

determining the weight of the material in the measuring container after the measuring container has been completely filled;

determining the bulk density of the material in the measuring container by dividing the weight of the material in the measuring container by the volume of the measuring container;

measuring the weight of the lot; and dividing the weight of the lot by the bulk density to obtain the volume of the lot.

2. The method according to claim 1, wherein the step of filling the measuring container creates a pouring cone of the material having a portion projecting beyond the inlet opening of the measuring container, and further comprising:

discontinuing the filling of the measuring container after the pouring cone reaches a predetermined height; and scraping off the projecting portion of the pouring cone with a scraping device.

3. The method according to claim 2, further comprising returning the scraped-off portion of the sample to the lot.

4. The method according to claim 1, wherein the step of determining the weight of the material in the measuring container comprises weighing an empty measuring container, weighing the measuring container after filling with sample, and determining the net weight of the sample in the measuring container by subtracting the weight of the empty measuring container from the weight of the filled measuring container, and emptying the measuring container.

5. The method according to claim 1, wherein the step of determining the weight of the material in the measuring container comprises emptying the measuring container of the material, and weighing the material.

6. The method according to claim 4, further comprising returning the sample of material to the lot after emptying the measuring container.

7. The method according to claim 5, further comprising returning the sample of material to the lot after weighing.

8. The method according to claim 1, wherein the lot is collected at a storage site and continuously conveyed from the storage site, and wherein the sample is collected from the material being conveyed.

9. The method according to claim 8, wherein the sample is collected using a mechanically-operating conveyor, and wherein the sample collected by the conveyor is ejected into an inlet of the screening plant.

* * * * *